United States Patent [19]

Tiitto

[11] Patent Number: 4,977,373
[45] Date of Patent: Dec. 11, 1990

[54] BARKHAUSEN NOISE METHOD FOR DETERMINING BIAXIAL STRESSES IN FERROMAGNETIC MATERIALS

[75] Inventor: Seppo I. Tiitto, Bethel Park, Pa.

[73] Assignee: American Stress Technologies, Inc., Pittsburgh, Pa.

[21] Appl. No.: 332,478

[22] Filed: Apr. 5, 1989

Related U.S. Application Data

[63] Continuation-in-part of Ser. No. 182,622, Apr. 18, 1988, abandoned.

[51] Int. Cl.[5] .................. G01B 7/24; G01R 33/12; G01R 35/00; G01N 27/72
[52] U.S. Cl. .................................. 324/209; 324/202
[58] Field of Search ................. 324/202, 209; 73/779

[56] References Cited

U.S. PATENT DOCUMENTS

| | | | |
|---|---|---|---|
| 3,427,872 | 2/1969 | Leep et al. | 324/209 X |
| 4,481,470 | 11/1984 | Wallace | 324/209 X |
| 4,528,856 | 7/1985 | Junker et al. | 324/209 X |
| 4,634,976 | 1/1987 | Tiitto | 324/209 X |
| 4,881,030 | 11/1989 | Stuecker et al. | 324/209 |

FOREIGN PATENT DOCUMENTS

0875271  10/1981  U.S.S.R. .............................. 324/209

OTHER PUBLICATIONS

Loomis, Keith E., *Barkhausen Biaxial Stress/Strain Measurement System*, Proceedings of the 13th International Nondestructive Testing Conf. San Antonio, Tex. 1981, 16 pages.

Karjalainen et al; "Detection of Fabrication Stresses by the Barkhausen Noise Method", The Effects of Fabrication Related Stresses on Product Manufacture and Performance (The Welding Institute, Abington Hall, Cambridge, 1985, sec. 13).

Furuya et al; Magnetic Barkhausen Noise Analysis in Bi-Axial Stress Test, Journal of Japanese Society of Nondestructive Inspection, vol. 36, No. 8, 1987, pp. 530–534.

*Primary Examiner*—Gerard R. Strecker
*Attorney, Agent, or Firm*—Kirkpatrick & Lockhart

[57] ABSTRACT

The present invention provides a method for determining biaxial stresses in a steel component by first generating a calibration datum from an experimental test piece having metallurgical properties similar to steel component and then applying values representative of measured Barkhausen noise levels obtained from the steel component to the calibration datum. The practice of the present invention yields values of strain in the first and second principal directions at the selected location on the steel component under examination.

5 Claims, 6 Drawing Sheets

BARKHAUSEN NOISE METHOD FOR DETERMINING BIAXIAL STRESSES IN FERROMAGNETIC MATERIALS

This a continuation-in-part application of U.S. Ser. No. 182,622, filed Apr. 18, 1988, abandoned.

BACKGROUND OF THE INVENTION

1. Field of the Invention

This invention relates to the evaluation of residual stresses in metal components; more particularly, to a method for determining biaxial stresses in steel components.

2. Description of the Prior Art

Stress and structural defects in ferromagnetic materials such as steel, as well as certain other properties of the metal piece, may be identified by creating a time-varying magnetic field within the metal piece and analyzing the magnetic noise created in the metal piece by the magnetic field. This detection technique employs a phenomenon known as the "Barkhausen effect" which has become well known to workers in the art as a series of abrupt changes or jumps in the magnetization of a substance when the magnetizing field created in the metal piece is gradually altered. An excellent background discussion of the Barkhausen effect appears in Leep et al. U.S. Pat. No. 3,427,872.

The abrupt jumps that occur in the magnetization as the intensity of the field is changed can be detected as electrical noise by a sensing coil disposed proximate or in contact with the metal piece. Several sensor configurations are described in Tiitto U.S. Pat. No. 4,634,976. The noise carried by the electrical leads from the sensing coil, commonly referred to as "Barkhausen noise", can be fed through a suitable processing network and, if desired, to an audio speaker. The level of the Barkhausen noise that is generated at a location within a metal piece depends in part on the sense, magnitude and direction of the stress or strain at that location and the microstructure of the metal. Accordingly, workers in the art have attempted to employ the Barkhausen effect and Barkhausen noise to identify stresses or strains and defects in and some microstructural characteristics of a metal piece.

Most systems that employ the Barkhausen effect to identify stresses or strains and defects in a metal piece include an energizing coil assembly and a sensing coil assembly. The energizing coil is disposed proximate the location of the metal piece under examination and is energized with a periodically time-varying signal to induce in the metal piece a periodically time-varying magnetic field. The resultant Barkhausen noise generated in the metal piece is sensed by the sensing coil and fed to circuitry which can process the noise in a variety of ways. Ultimately, the processed Barkhausen noise is fed to a device for display. The Barkhausen noise is referred to herein in terms of an MP (magnetoelastic parameter) value, which is proportional to the level of Barkhausen noise measured within a specified frequency range.

In conventional practice of testing stresses in a metal piece, Barkhausen noise levels (MP values) are put to practical use by first preparing uniaxial calibration curves from test pieces of each grade of steel to be examined; making actual measurements of MP values in the steel component to be tested; and comparing the MP values derived from the actual measurements against the appropriate uniaxial calibration curve to determine the stresses or strains present at the test location on the steel component. A uniaxial calibration curve is obtained by stressing a test piece in compression and tension in one (axial) direction only and ignoring the stresses in other directions or assuming that they are very small. The MP value measured under each condition of compression or tension constitutes a representation of the stress/strain present along the axis of loading. Such measurements are valid as long as they are performed within the elastic region of the test piece.

Workers in the art have reported wide variations between stress/strain measurements made by the Barkhausen noise calibration curve method just described and other stress/strain measurement methods. In most cases, it has been assumed that such variations can be related to differences in the microstructural variables of steel, such as composition, texture, grain size, deformation and metallurgical structure. However, virtually all practical steel components (i.e., welded, fabricated components) have a complex biaxial residual stress condition created by the steel manufacturing process, and enhanced and modified by subsequent fabrication, welding and machining processes; these are the important residual stresses that manufacturers and users of steel components seek to determine. As will be apparent from the description that follows, application of uniaxial calibration to test biaxial stress/strain condition may lead to errors that may be larger than those resulting from typical microstructural variation within a specified steel grade.

The concept of biaxial, or plane, stress/strain condition is well understood. According to the linear elasticity theory and Hooke's law, every plane strain condition can be expressed in terms of two principal normal strains ($\epsilon_1$, $\epsilon_2$) which are perpendicular to one another, and one principal out-of-plane normal strain ($\epsilon_3$) perpendicular to the surface:

$$\epsilon_1, \epsilon_2 = \frac{\epsilon_x + \epsilon_y}{2} \pm \sqrt{\left(\frac{\epsilon_x - \epsilon_y}{2}\right)^2 + \left(\frac{\gamma xy}{2}\right)^2} \quad (1),(2)$$

$$\epsilon_z = \epsilon_3 = -\frac{\nu}{1-\nu}(\epsilon_x + \epsilon_y) \quad (3)$$

where x and y are randomly selected coordinates in the sample plane, $\epsilon_x$, $\epsilon_y$ are normal strains measured in x and y directions, $\gamma xy$ is the shear strain in the xy sample plane; and $\nu$ is the Poisson ratio.

Two principal normal stresses ($\sigma_1$, $\sigma_2$) of biaxial plane stress condition may be easily found by the expressions:

$$\sigma_1 = \frac{E}{1-\nu^2}(\epsilon_1 + \epsilon_2) \quad (4)$$

$$\sigma_2 = \frac{E}{1-\nu^2}(\epsilon_2 + \epsilon_1) \quad (5)$$

where E is modulus of elasticity.

It may be noted that, by definition, a free surface cannot support normal stresses perpendicular to the surface plane, i.e., $\sigma_3 = 0$; normal strain $\epsilon_3$ may still exist, however, due to Poisson's effect.

For engineering applications, strains $\epsilon_1$, $\epsilon_2$ and stresses $\sigma_1$, $\sigma_2$ are commonly evaluated using a blind hole drilling method or X-ray diffraction. Both of these techniques are often considered time consuming and less practical.

The conventional application of uniaxial calibration, using Barkhausen noise as described above, to test biaxial plane stress/strain conditions may lead to serious errors, sometimes in the order of magnitude of 50-100%. If, for example, in employing the uniaxial calibration method, a certain MP value is measured on a structural component, that MP value is applied to a calibration curve, which assumes transverse strain ($\epsilon_2$) to be zero, to yield a certain value of longitudinal strain ($\epsilon_1$). Actually, however, the transverse strain in a structural component may have a large value, and the use of a calibration curve generated at the actual value of transverse strain would produce a longitudinal strain markedly different from the value derived from the use of the aforementioned calibration curve that assumes transverse strain to be zero. It is this possibility of both principal strain components being large that creates concern for manufacturers and users of structural components and that makes the uniaxial calibration method unreliable or even dangerous.

Accordingly, there exists a need to develop a Barkhausen noise method for better determining biaxial stress conditions in practical steel components. To date, there has been little recognition by workers in the art that biaxial residual stress distribution may actually be a major factor affecting Barkhausen noise testing. For example, in an article entitled "Barkhausen Biaxial Stress/Strain Measurement System" by K. Loomis, Proceedings of the 13th International Nondestructive Testing Conference (San Antonio, Texas 1981), data is provided from experiments in which there was little transverse stress in the principal directions under evaluation; from that data, the conclusion is advanced that no correction for biaxial stress is needed. In an article entitled "Detection of Fabrication Stresses by the Barkhausen Noise Method" by L. Karjalainen et al., The Effects of Fabrication Related Stresses on Product Manufacture and Performance (The Welding Institute, Abington Hall, Cambridge 1985), § 13, p. 1, the authors acknowledge the importance of biaxial residual stresses and present data on their influence on uniaxial calibration curves, yet suggest no procedure for evaluating the effects of the presence of biaxial residual stresses. In an article entitled "Magnetic Barkhausen Noise Analysis in Bi-Axial Stress Test" by Furuya et al., *Journal of Japanese Society of Nondestructive Inspection*, Vol. 36, No. 8 (1987), p. 530, the authors make an attempt to directly evaluate biaxial stresses with the Barkhausen noise method, but conclude that the noise can be related only to the difference in each principal stress.

SUMMARY OF THE INVENTION

The object of the present invention is to provide a Barkhausen noise method for determining biaxial stresses in steel components by eliminating or significantly reducing error due to the effect of transverse stress/strain on Barkhausen noise levels by taking into account any combination of transverse and longitudinal stresses (strains).

Accordingly, the present invention provides a method for determining biaxial stresses in a steel component comprising the steps of: (a) generating a calibration datum (i) from an experimental test piece having metallurgical properties similar to said steel component and (ii) within the elastic limits of said test piece, said calibration datum reflecting varying Barkhausen noise levels as both longitudinal and transverse strains are varied relative to their zero values; (b) measuring Barkhausen noise levels in the first and second principal directions at a selected location on said steel component; and (c) using said calibration datum, converting said measured Barkhausen noise levels to values of longitudinal and transverse strain in the first and second principal directions at said selected location on said steel component. The practice of the present invention yields values of strain in the first and second principal directions at the selected location on the steel component under examination; these strain values may be easily converted to stress values by the conventional formulae (4), (5) set forth above.

In the preferred embodiment of the present invention, accurate values of longitudinal and transverse strain in the principal directions at the selected location on the steel component under examination are produced by converting a pair of MP values measured in the first and second principal directions through calibration datum directly into values of strain or stress in said principal directions.

In a second embodiment of the invention, an approximation of longitudinal and transverse strain in the first and second principal directions at the selected test location is produced. The approximation is made by first applying values representative of measured Barkhausen noise levels to the calibration datum at zero transverse strain to obtain an approximation of the values of strain in the first and second principal directions. Then, by use of the calibration datum, (i) the approximation of strain in the first principal direction is corrected by applying thereto the transverse effect of that approximation in the second principal direction; and (ii) the approximation of strain in the second principal direction is corrected by applying thereto the transverse effect of that approximation in the first principal direction.

The term "calibration datum" as used herein means a collection of numerical information representing the interdependence of noise levels expressed in MP units, transverse strain or stress, and longitudinal strain or stress. Because strain can be measured directly with strain gages, it is conveniently used as the variable instead of stress. The calibration datum C which is generated by establishing experimental points produced from the biaxial loading of a test piece as more fully described below and conforming to the expression $$C = f(MP, \epsilon_L, \epsilon_T) \qquad (6)$$

wherein
f is an experimental function and MP,
$\epsilon_L$ and $\epsilon_T$ represent cartesian coordinates;
MP = magnetoelastic parameter proportional to the Barkhausen noise level, measured within a specific frequency range,
$\epsilon_L$ = longitudinal strain,
$\epsilon_T$ = transverse strain,
may take a variety of forms including a table or a graphic form, either two-dimensional or three-dimensional. In two-dimensional form, the calibration datum may be a series of longitudinal or transverse MP vs. strain curves at specified values of transverse or longitudinal strain; in three-dimensional form, the calibration datum may be a three-dimensional surface reflective of MP as a function of longitudinal and transverse strain.

From the descriptions below, workers skilled in the art will be able to generate a calibration datum for use in the practice of the present invention by the use of known techniques including the use of known computer-assisted plotting methods.

Further details and advantages of the present invention will become apparent from the detailed description of the preferred embodiments that follows, taken together with the accompanying drawings in which:

DETAILED DESCRIPTION OF THE PREFERRED EMBODIMENTS

A. Preparation of the Calibration Sample

Sample Characteristics

In order to ensure that the calibration datum and thus the ultimate test results are as accurate as possible, the calibration sample should represent the component to be tested as closely as possible. Accordingly, the following factors should be considered:

(a) The microstructure of the calibration sample should correspond to that of the actual material to be tested. This means that heat treatment, composition, hardness and other steel manufacturing parameters should be the same for the calibration sample and the component to be tested.

(b) The surface finish of the calibration sample should mimic the component to be tested. Painted or oxidized surfaces should be cleaned to bare metal by fine sandpaper. Whether the surface of the test component is ground, machined or shot peened, the calibration sample surface should be prepared the same way or cut from the actual test component.

Sample Preparation

Figure 1:
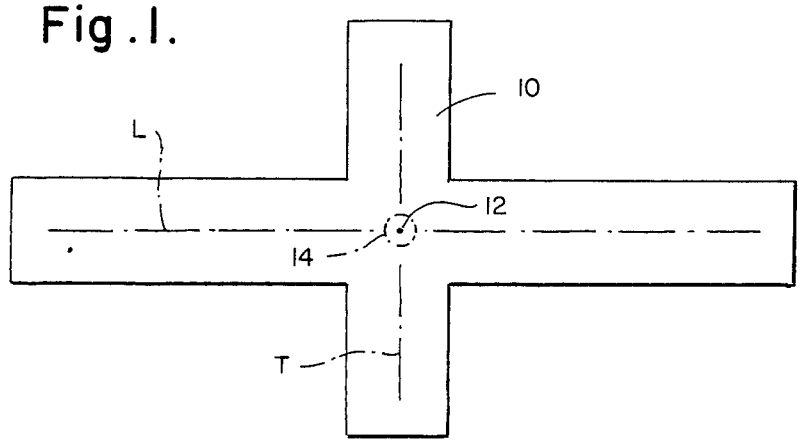
FIG. 1 is a top plan view of a calibration test piece with an indication of a central test location.
Figure 2:
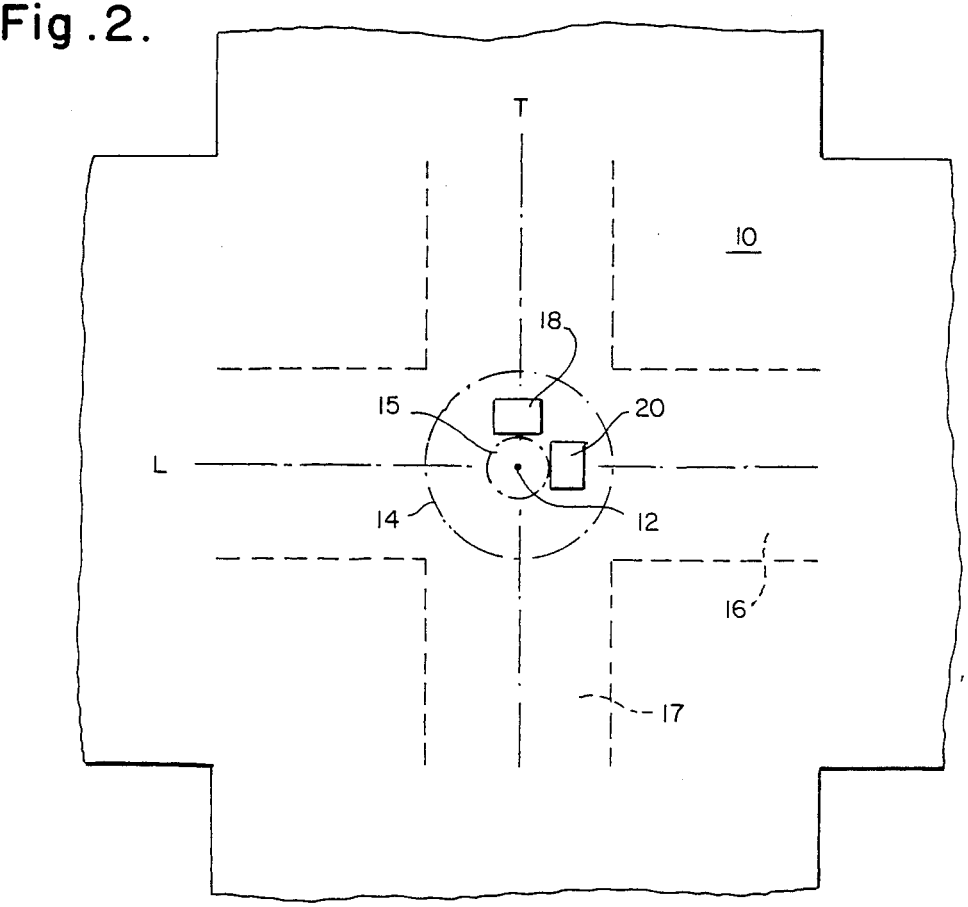
FIG. 2 is an enlarged view of the test location of FIG. 1 showing the location of strain gages.
Figure 3:
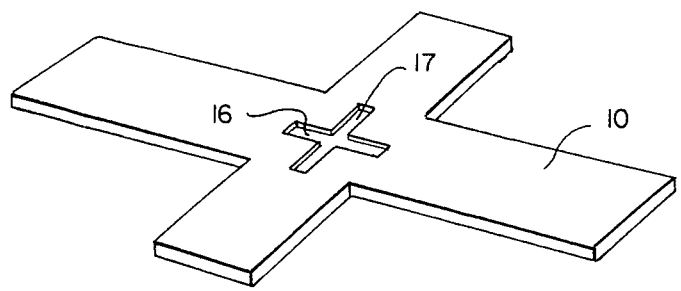
FIG. 3 is an isometric view of the bottom of the test piece shown in FIG. 1.

Referring to the drawings, particularly to FIGS. 1-3, there is shown a calibration sample 10 suitable for use in generating experimental data from which the calibration datum of the present invention may be constructed. Calibration sample 10 preferably is in the form of a cross and is intended to be held in a suitable fixture for the application of controlled tensile and compression loads within the elastic range about the midpoint 12 of its longitudinal axis (L) and transverse axis (T). If the rolling direction is known, it should be parallel to one of the axes.

The dimensions of calibration sample 10 may vary but one set of dimensions would be a thickness of 6 mm, a leg length of 100 mm and a width of each leg portion of 20 mm. A central test area having a diameter of 6 mm is designated by the reference numeral 14; within test area 14 is test location 15 having a diameter of about 2 mm (see FIG. 2). In order to assure a biaxial stress field as controllable as possible and to focus it in the area 14, axial grooves 16, 17 in the form of a cross centered on midpoint 12 are machined to a depth of about 2 mm in the bottom of test piece 10 (see FIG. 3). Each groove has a length of 30 mm.

As shown in FIG. 2, small longitudinal and transverse strain gages 18, 20, respectively, of any well-known type are mounted on the surface of test area 14, just outside of test location 15. It will be noted that longitudinal strain gage 18 is aligned with the transverse axis (T) and transverse strain gage 20 is aligned with the longitudinal axis (L), the latter being parallel to the rolling direction if known. The accuracy of the readings obtained by strain gages 18, 20 may be checked by affixing additional strain gages (not shown) on both axes within test location 15 in the orientation just described.

Strain data is generated from calibration sample 10 by mounting it in a biaxial bending fixture and applying controlled loads in tension and compression to the longitudinal and transverse portions of sample 10 by bending them as if each of those portions were independent of one another. The exact configuration of the biaxial bending fixture is not critical; it will be appreciated by persons skilled in the art that any suitable configuration may be used that permits such bending of each leg of the calibration sample independent of the other leg. At each condition of loading, Barkhausen noise is measured within test location 15 in the magnetizing directions of the longitudinal and transverse axes. These measurements may be made by any suitable Barkhausen noise sensing system such as the sensing and energizing coil and core assemblies described in Tiitto U.S. Pat. No. 4,634,976 which is incorporated herein by reference.

B. Optimizing Magnetic Field Strength Of The Barkhausen Noise Sensing System A Barkhausen noise sensing system should have a control to adjust the strength of the magnetic field generated in the calibration sample. For example, the STRESSCAM 500C, manufactured by American Stress Technology, Inc., has a control marked MAGN. If the magnetic field strength generated in the calibration sample is too high, either the sample or the sensor's magnetizing circuit may become magnetically saturated. As this condition is approached, the sensitivity of the system becomes impaired. Conversely, when magnetic field strength is too low, sufficient signal levels for detection may not be reached and/or the measurement range may be limited. Therefore, it is desirable to determine the optimal value of magnetic field strength corresponding to the optimal stress sensitivity before generating calibration data from the calibration sample.

Optimization of magnetic field strength involves a determination of the greatest slope of the curve of stress vs. MP when the calibration sample is subjected to both tension and compression. The determination may be accomplished by (i) slowly increasing the compression to which one leg of the calibration sample is subjected until the rate of change of MP slows, (ii) in that condition, varying the magnetic field strength and recording MP values, (iii) repeating the procedure while the leg of the calibration sample is subjected to tension, and (iv) calculating the ratio MP tension/MP compression at each field strength setting. The setting of magnetic field strength at the highest ratio of MP tension/MP compression is used as the optimal setting.

With the magnetic field strength set at the optimal value, MP is measured in the L and T directions with no load in either direction. These readings will be referred to hereinafter as $MP_L$ and $MP_T$.

C. Determination of Elasticity Limits And Zero Strain Point

In generating information from the calibration sample for the calibration datum, the elastic range of the calibration sample should not be exceeded either in tension or compression. Exceeding elasticity limits results in plastic deformation of the calibration sample which, in turn, may change the residual stress state of the sample with the consequent collection of incorrect data. Further, residual stresses in actual components cannot in principle exceed the elasticity limit which normally is 40-60% of the nominal 0.2% yield strength of the material.

The procedure for determining the elasticity limits of an isotropic material is as follows:

1. The magnetizing strength control of the sensor system is set at the optimal value determined in accordance with the above-described technique. The strain gages of the calibration sample are set to read zero in both directions ($\epsilon_L = \epsilon_T = 0$).

2. Tensile strain in the L direction is increased in steps of approximately 10% of the nominal 0.2% yield strength of the material. The corresponding MP readings are recorded commencing with $MP_L$, which is the no load reading for MP. After each step, the load is released until the strain gage reads zero and the MP reading is again recorded. The elasticity limit will not have been exceeded so long as the MP at the zero strain gage reading after each step differs from $MP_L$ by less than approximately 3%. When the elasticity limit has been exceeded, the strain cycle is not reversible and compressive residual stresses will have been created as a result of plastic strain. It now will have been determined that the elasticity limit lies between the last two strain steps.

Figure 4:
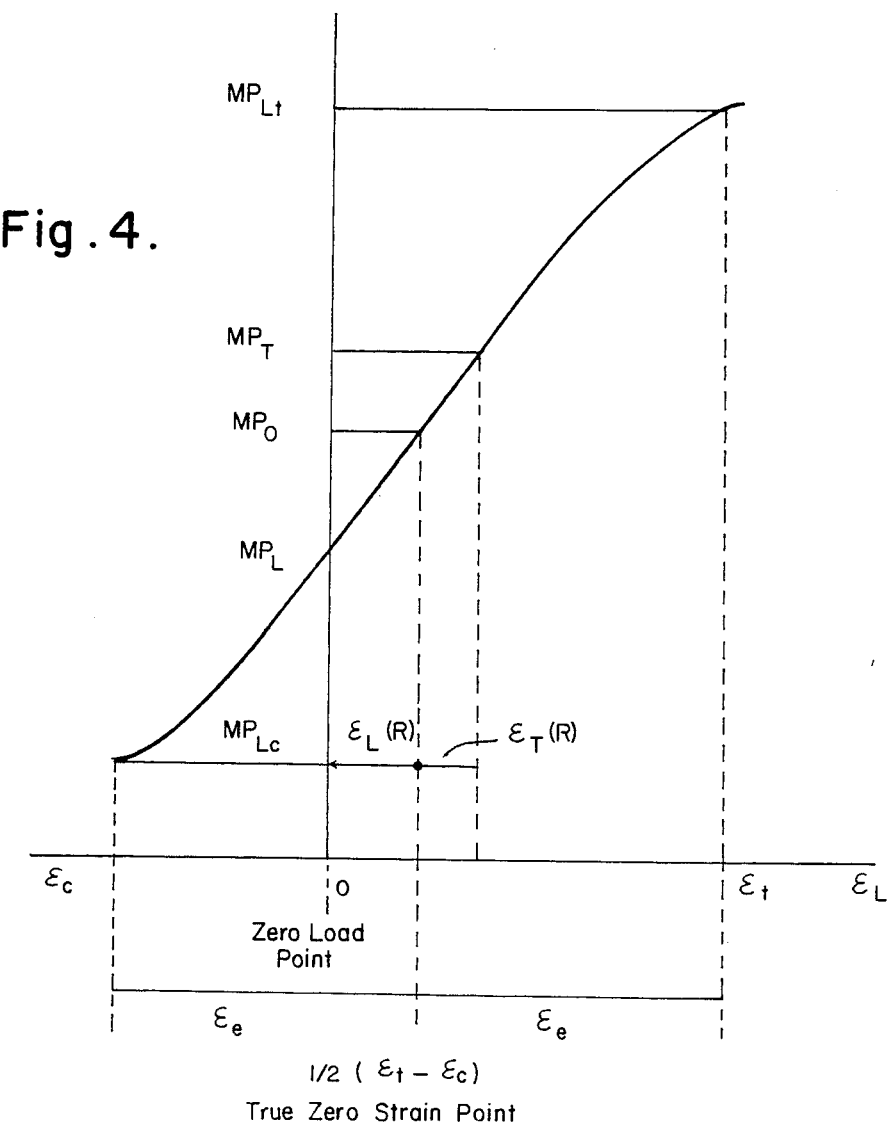
FIG. 4 is a plot of a uniaxial strain curve indicating zero strain point and the elastic limits in tension and compression.

3. To evaluate the elasticity limit more precisely, the new residual stresses created above may be compensated for by bending the L leg of the calibration sample until $MP = MP_L$. The strain gage is reset to read zero and step 2 is repeated in small increments between the last two strain steps of step 2. An approximate decrease of 3% in $MP_L$ may again be used to indicate the elasticity limit. Then mark as shown in FIG. 4:

$MP_{Lt}$ = MP reading at elasticity limit in tension $\epsilon_T$ = strain gage reading at elasticity limit in tension 4. The elasticity limit of the calibration sample in compression is next determined. First, the new residual stresses are compensated for as in step 3. Next, the strain gage is reset to zero and steps 2 and 3 are repeated to determine:

$MP_{Lc}$ = MP reading at elasticity limit in compression $\epsilon_c$ = strain gage reading at elasticity limit in compression (negative number).

5. A uniaxial strain curve MP vs. $_L$ is prepared as shown in FIG. 4 with apparent (no load) zero point indicated by 0. The true zero strain point is next determined. Because it is essentially located symmetrically between the elasticity limits in tension and compression, the true zero strain point may be determined by the expression:

$$\epsilon_e = \tfrac{1}{2}(\epsilon_t - \epsilon_c) \qquad (7)$$

By projecting the zero strain point to the curve and moving horizontally to the MP axis, the value of $MP_o$, which is the MP value at true zero strain may be determined. An approximation of $MP_o$ may be expressed by the formula:

$$MP_o = MP_{Lc} + \tfrac{1}{2}(MP_{Lt} - MP_{Lc}) \qquad (8)$$

FIG. 4 also provides the basis for determining longitudinal residual strain according to the expression:

$$\epsilon_L(R) = \epsilon_e - \epsilon_t \qquad (9)$$

This is the strain corresponding to $MP_L$ on a true strain scale and determines the shift from the apparent (no load) uniaxial strain scale to the true (no strain) scale. In the case of an isotropic material, the uniaxial stress curve produced in the transverse (T) direction will be identical to the curve in the L direction (FIG. 4). Thus, transverse residual strain $\epsilon_T(R)$ is the strain corresponding to $MP_T$ on the true strain scale (see projection on FIG. 4).

6. Because the MP value at $MP_o$ is now known for the L and T directions, legs L and T of the calibration sample are bent until $MP = MP_o$ is measured simultaneously in both directions. The L and T strain gages are reset to zero. In this situation, test location 15 on the calibration sample is in a near true zero stress condition. Residual strains $\epsilon_L(R)$ and $\epsilon_T(R)$ can be converted into residual stresses using the conventional equations. However, if $MP_o$ differs more than 15% from $MP_L$ or $MP_T$, steps 2 through 6 above should be repeated to correct for the effect of transverse residual strain that was present when performing those steps and to determine again $\epsilon_e$, $MP_o$, $\epsilon_L(R)$ and $\epsilon_T(R)$.

Figure 5A:
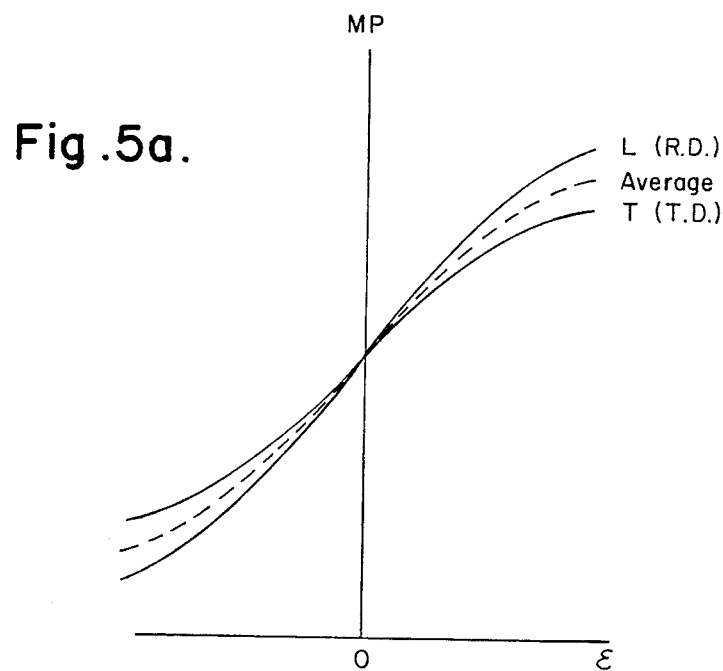
FIG. 5a is a plot of uniaxial strain curves in the rolling direction and the transverse direction when the material has mild anisotropy.
Figure 5B:
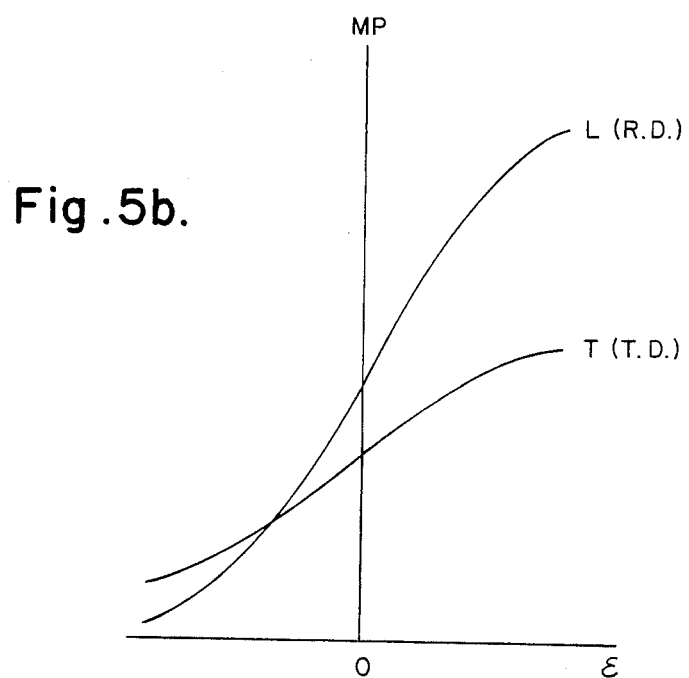
FIG. 5b is a plot of uniaxial strain curves in the rolling direction and the transverse direction when the material has strong anisotropy.

If the steel component to be tested (and thus the calibration sample) exhibits anisotropy, the uniaxial strain curves may vary in different directions. For example, if mechanical properties (including elasticity limits) are different between the rolling direction (R.D.) and the transverse direction (T.D.), magnetoelastic anisotropy may be expected to appear in their respective strain curves as shown in FIGS. 5a and 5b. In such case, steps 1 through 6 above should be conducted independently for the L and T directions; the deviation between the curves so developed may be used as a measure of anisotropy. It should be noted that for certain types of anisotropy, $MP_o$ may have different values for the L and T directions as in FIG. 5b.

D. Preferred Embodiment
Generation Of Biaxial Calibration Data

The preferred embodiment of the present invention involves the generation of a calibration datum from the calibration sample after its test location has been placed in the condition of zero strain. Thus, steps 1 through 6 described above are practiced to achieve that condition. By bending of the calibration sample, values of MP in the longitudinal direction, MP(L), and the transverse direction, MP(T), are determined at predetermined increments of $\epsilon_T$ and $\epsilon_L$ and these values are placed in tabular form, as described in detail below. It is convenient to design the table to have either seven increments of $\epsilon_T$ and $\epsilon_L$ (called a 7×7 table) or nine increments of $\epsilon_T$ and $\epsilon_L$ (called a 9×9 table). An example of a 7×7 table is shown below as Table I; in Table I, $\epsilon_e = 1000\mu\epsilon$:

TABLE I

| | | 900 | | 600 | | 300 | | 0 | | −300 | | −600 | | −900 | |
|---|---|---|---|---|---|---|---|---|---|---|---|---|---|---|---|
| | | L | T | L | T | L | T | L | T | L | T | L | T | L | T |
| j | 900 | xx | | | | | | | | | | | | xx | |
| | 600 | | | | | | | | | | | | | | |
| | 300 | | | | | | | | | | | | | | |
| | 0 | | | | | | | $MP_o$ | $MP_o$ | | | | | | |
| | −300 | | | | | | | | | | | | | | |
| | −600 | | | | | | | | | | | | | | |
| | −900 | xx | | | | | | | | | | | | xx | |

Even incremental values of strain in Table I are selected (e.g., 300, 600, 900, etc.) and in a way to avoid $\epsilon_e$ being exceeded. The maximum value of $\epsilon_T$ and $\epsilon_L$ used in Table I represents 90% of the elasticity limit.

(a) ISOTROPIC MATERIAL

The data for the tabular calibration datum is generated by bending the L and T legs of the calibration sample until $MP = MP_o$; then the strain gages are reset to zero. MP is measured in the L direction at each (i, j) combination of $\epsilon_L$, $\epsilon_T$ and the readings are inserted into the L column of Table I. Measurements are continued by moving systematically from column to column by varying $\epsilon_L$ first, then changing $\epsilon_T$ and so on. After each step of varying $\epsilon_L$, $\epsilon_T$ is checked and readjusted to compensate for transverse contraction/expansion due to the Poisson effect.

It should be noted that strain combinations at the extreme corners of the calibration datum (shown as "xx" on Table I) are avoided in making the measurements. These combinations should be extrapolated instead, as they are likely to result in plastic deformation and an undesirable shift in the zero strain point.

An example of a 7×7 table with the L columns filled in is shown in Table II below. The vertical columns of Table II describe the change of MP(L) as a function of longitudinal strain and the horizontal columns describe the change of MP(L) as a function of transverse strain.

TABLE II

| | | 900 | | 600 | | 300 | | 0 | | −300 | | −600 | | −900 | |
|---|---|---|---|---|---|---|---|---|---|---|---|---|---|---|---|
| | | L | T | L | T | L | T | L | T | L | T | L | T | L | T |
| j | 900 | xx | | 250 | | 260 | | 260 | | 257 | | 248 | | xx | |
| | 600 | 191 | | 215 | | 239 | | 239 | | 238 | | 227 | | 218 | |
| | 300 | 145 | | 161 | | 200 | | 216 | | 211 | | 198 | | 190 | |
| | 0 | 116 | | 125 | | 146 | | 168 | | 167 | | 161 | | 155 | |
| | −300 | 101 | | 105 | | 109 | | 114 | | 121 | | 121 | | 120 | |
| | −600 | 88 | | 90 | | 91 | | 93 | | 96 | | 93 | | 90 | |
| | −900 | xx | | 84 | | 82 | | 80 | | 78 | | 76 | | xx | |

Next, the T columns of Table II may be filled in with MP(T) readings by performing a simple conversion of the readings in the L column. The basis for the conversion is that the uniaxial stress curves for isotropic materials are the same in both the L and T directions. The conversion may be expressed as follows:

$$MP(L)(i,j) = MP(T)(j,i) \tag{10}$$

where $i, j = +900, +600 \ldots -600, -900$ (in Table II) The effect of the conversion is to utilize readings measured in one principal direction (L) for testing two principal directions (L,T); i.e., to obtain a combination of MP(L), MP(T) for each combination of $\epsilon_L$, $\epsilon_T$.

Conversion (10) has the same effect as separate measurement of both MP(L) and MP(T) at each combination of $\epsilon_L$, $\epsilon_T$ (which is an alternate way of completing Table II). An example of the conversion at strain combination $-600, +300\mu\epsilon$ is given below:

Test $-600, +300\mu\epsilon$ in the L direction only (Table II):

$MP(L) = 198$ when $\epsilon_L = 300$, $\epsilon_T = -600$ $MP(L) = 91$ when $\epsilon_L = -600$, $\epsilon_T = 300$ = Equivalent to testing same separately in L and T directions:

= Equivalent to testing same separately in $L$ and $T$ directions:

$$MP(L) = 198 \brace MP(T) = 91 \text{ when } \epsilon_L = 300, \epsilon_T = -600$$

= Conversion:

| L | T |
|---|---|
| 198 | 91 |

Table III below represents a 7×7 table completed in accordance with this principle.

TABLE III

| | | 900 | | 600 | | 300 | | 0 | | −300 | | −600 | | −900 | |
|---|---|---|---|---|---|---|---|---|---|---|---|---|---|---|---|
| | i | L | T | L | T | L | T | L | T | L | T | L | T | L | T |
| j | 900 | xx | xx | 250 | 191 | 260 | 145 | 260 | 116 | 257 | 101 | 248 | 88 | xx | xx |
| | 600 | 191 | 250 | 215 | 215 | 239 | 161 | 239 | 125 | 238 | 105 | 227 | 90 | 218 | 84 |
| | 300 | 145 | 260 | 161 | 239 | 200 | 200 | 216 | 146 | 211 | 109 | 198 | 91 | 190 | 82 |
| | 0 | 116 | 260 | 125 | 239 | 146 | 216 | 168 | 168 | 167 | 114 | 161 | 93 | 155 | 80 |
| | −300 | 101 | 257 | 105 | 238 | 109 | 211 | 114 | 167 | 121 | 121 | 121 | 96 | 120 | 78 |
| | −600 | 88 | 248 | 90 | 227 | 91 | 198 | 93 | 161 | 96 | 121 | 93 | 93 | 90 | 76 |
| | −900 | xx | xx | 84 | 218 | 82 | 190 | 80 | 155 | 78 | 120 | 76 | 90 | xx | xx |

It may be noted that the symmetric MP combinations at the diagonal line $\epsilon_T = \epsilon_L$ represent biaxial calibration for the hydrostatic stress/strain state, and those at $\epsilon_T = 4\epsilon_L$ approximate stresses on the surface of an ideal cylinder ($\epsilon_T = 4.25 \epsilon_L$).

(b) ANISOTROPIC MATERIAL

The effect of mild anisotropy with elasticity limits $\epsilon_e$ and zero strain MP readings $MP_o$ approximately equal in both L(R.D.) and T(R.D.) directions (as in FIG. 5a) can be minimized by evaluating the calibration datum, Table II, separately for the L and T directions and using the average for each column to complete the final table, Table III.

The effect of strong anisotropy with different zero strain MP readings in L and T directions (as in FIG. 5b) and possibly different elasticity limits can be accounted for by including the anisotropy in the calibration datum. This is accomplished by selecting the incremental values of $\epsilon_L$ and $\epsilon_T$ to reflect different elasticity limits in L(R.D.) and T(T.D.) directions and testing MP(L) and MP(T) separately at each combination of $\epsilon_L$, $\epsilon_T$. Depending on the steel manufacturing process, other directions of anisotropy than R.D. and T.D. may be defined. Conversion (10) which applies only to isotropic (symmetric) material behavior, cannot be used in this case.

Table IV below represents a 7×7 table completed for strongly anisotropic material in this way. Limitations in the use of anisotropic calibration datum is discussed below.

Use Of The Calibration Datum

A calibration datum, represented by the information set forth in Tables III and IV, is used in accordance with the present invention to convert MP readings measured in actual components into stresses/strains. That conversion is accomplished by first cleaning the test area of the component to bare metal by fine sandpaper. The settings of the sensor system should be the same as those used in generating the calibration datum. The MP values are tested in different angles on the component surface at the test location until the highest MP reading is found; this reading denotes Barkhausen noise level in the first principal direction, $MP_1$. Next, the lowest MP reading is measured 90° to the first principal direction and that reading denotes Barkhausen noise level in the second principal direction, $MP_2$. The calibration datum table is then referenced to match the pair of measured MP readings, $MP_1$, $MP_2$ with the (nearest) combination of readings and corresponding strains in the table.

For example, by reference to Table III:

| | | |
|---|---|---|
| $MP_1 = 238$ | $\epsilon_1 = +600$ | $\sigma_1 = 112$ MPa |
| $MP_2 = 105$ | $\epsilon_2 = -300$ | $\sigma_2 = 26$ MPa |
| $MP_1 = 185$ | $\epsilon_1 = +150$ | $\sigma_1 = 6$ MPa |
| $MP_2 = 105$ | $\epsilon_2 = -410$ | $\sigma_2 = -80$ MPa |

Strains have been converted into stresses using the formulae (4), (5) above. In the last example, strains were determined by extrapolating between the nearest combinations found in Table III. A more finely divided table, such as a 9×9 table would assist in making such extrapolations.

If needed, the third principal strain component $\epsilon_e$ perpendicular to the surface can be found by the expression (3) set forth above.

In the case of strongly anisotropic material as in Table IV, readings $MP_1$ and $MP_2$ are measured in actual components of the same material in the same directions relative to anisotropy, as those in which the calibration datum was constructed. Typical such directions are R.D. and T.D. in sheet material, axial and circumferential directions in (drawn) pipes, longitudinal and trans-

TABLE IV

| | | 1650 | | 1100 | | 550 | | 0 | | −550 | | −1100 | | −1650 | |
|---|---|---|---|---|---|---|---|---|---|---|---|---|---|---|---|
| | i | L | T | L | T | L | T | L | T | L | T | L | T | L | T |
| j | 1050 | xx | xx | 428 | 84 | 410 | 86 | 380 | 88 | 318 | 108 | 238 | 103 | xx | xx |
| | 700 | 358 | 71 | 377 | 74 | 364 | 74 | 320 | 82 | 240 | 109 | 169 | 107 | 107 | 125 |
| | 350 | 322 | 57 | 320 | 61 | 295 | 67 | 226 | 74 | 143 | 100 | 102 | 115 | 62 | 135 |
| | 0 | 252 | 43 | 239 | 48 | 205 | 56 | 123 | 73 | 80 | 97 | 56 | 117 | 43 | 141 |
| | −350 | 154 | 30 | 130 | 36 | 100 | 50 | 53 | 76 | 39 | 91 | 37 | 127 | 37 | 149 |
| | −700 | 62 | 22 | 48 | 30 | 38 | 47 | 31 | 79 | 30 | 91 | 32 | 133 | 35 | 155 |
| | −1050 | xx | xx | 23 | 28 | 23 | 45 | 24 | 79 | 26 | 96 | 30 | 134 | xx | xx | verse directions in turbine blades, etc. For example, if calibration datum was determined for an anisotropic pipe grade with L as axial, T as circumferential direction, $MP_1$ and $MP_2$ should be measured in actual components of the same pipe grade in axial and circumferential directions as well.

Accordingly, error can be involved in biaxial calibration of strongly anisotropic materials if (i) such directions of anisotropy are not known in actual components or (ii) principal stress directions in actual components differ significantly from L and T directions of calibration sample (datum).

It will be apparent to those skilled in the art that a computer may be used to generate a much more finely divided table for use as the calibration datum and to perform more and more accurate conversions into stresses and strains.

E. Alternate Embodiment

The present invention may also be practiced by use of an approximation technique rather than by use of direct conversion from the calibration datum table as described above. In this alternate embodiment, care is taken, as well, to assure that measurements are made within the elastic limits of the calibration sample and that the zero strain point is determined as in the preferred embodiment.

Generation Of Biaxial Calibration Data

The alternate embodiment of the present invention involves the generation of a calibration datum in the same manner as that described in the preferred embodiment except that only MP(L) measurements are used to construct the calibration datum.

In this alternate embodiment, data points are generated for MP(L) by varying $\epsilon_L$ at various specified intervals of $\epsilon_T$, the same as in the preferred embodiment.

Figure 6:
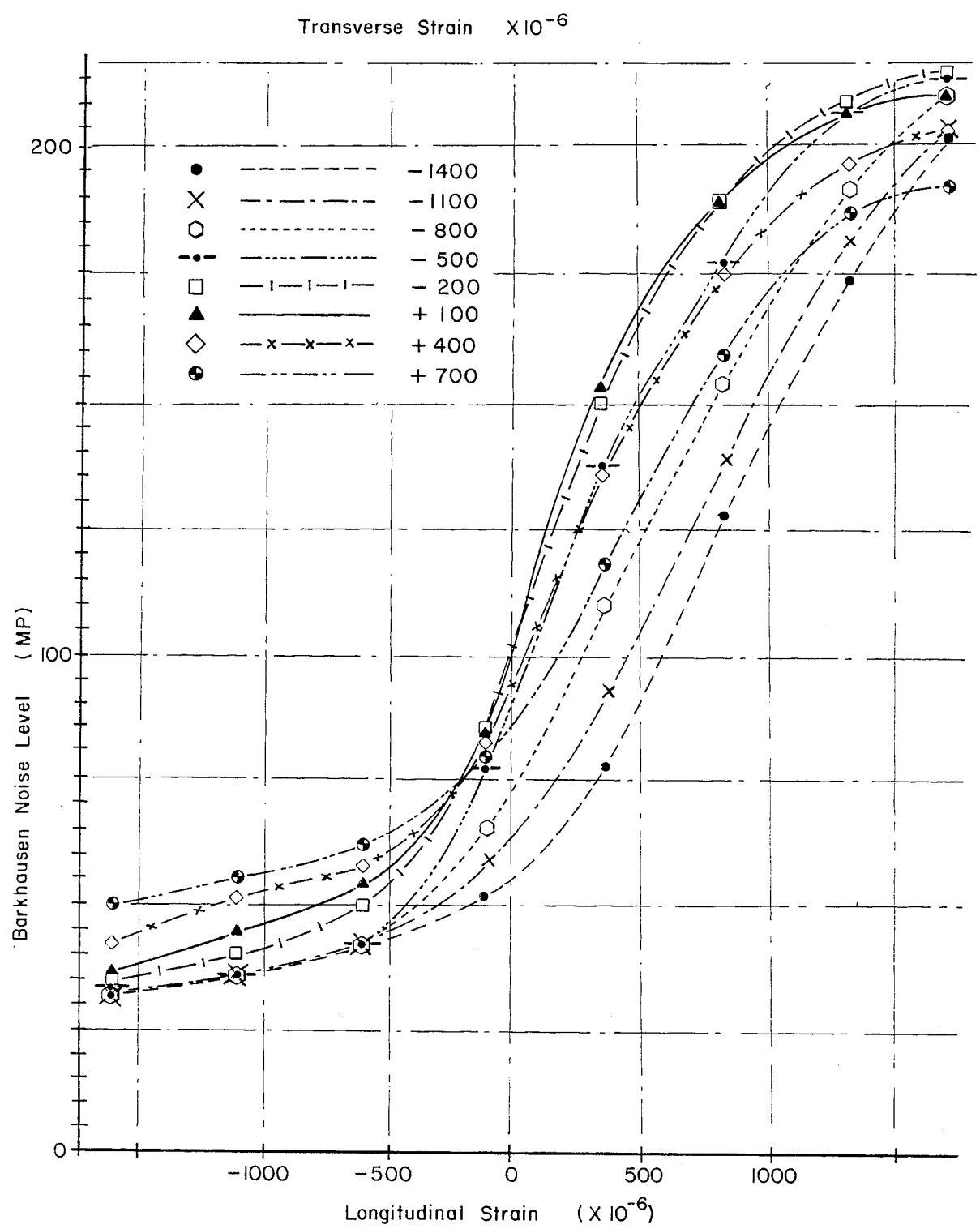
FIG. 6 is a plot of longitudinal strain calibration curves having eight different values of transverse loading.
Figure 7:
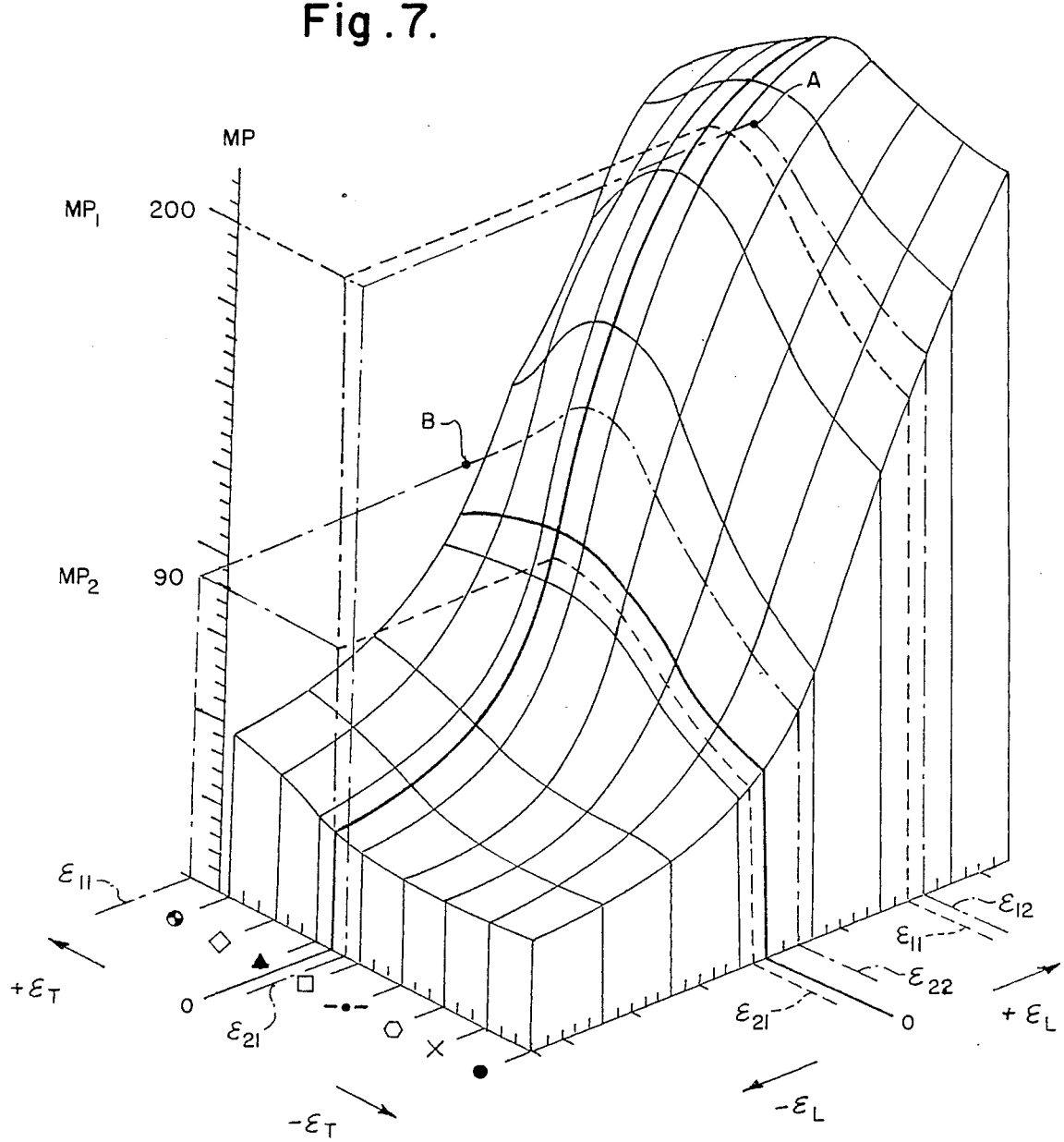
FIG. 7 is an isometric view of a calibration surface datum generated from the curves shown in FIG. 6 and used in the explanation of Example I.
Figure 8:
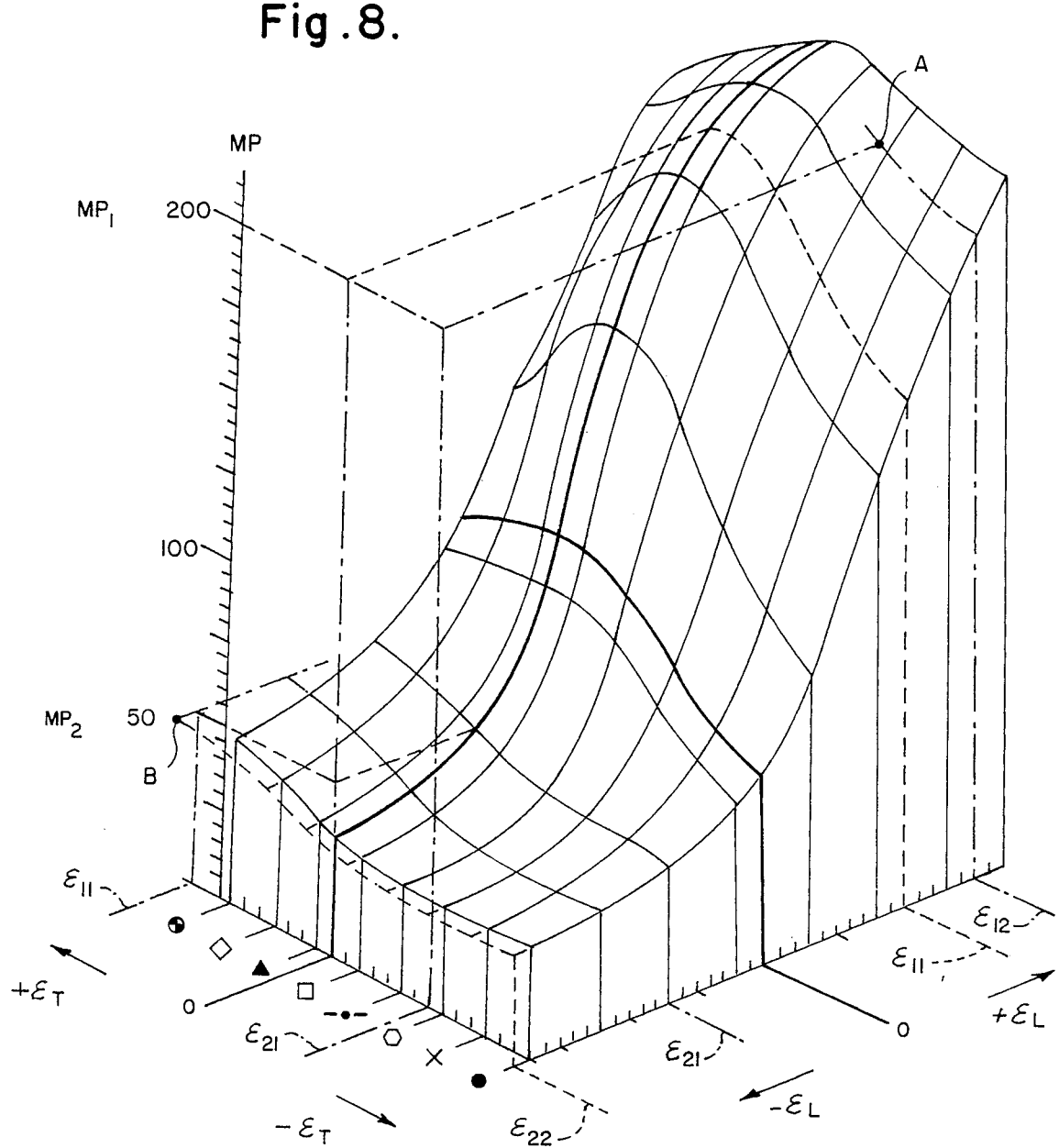
FIG. 8 is an isometric view similar to FIG. 7 and used in the explanation of Example II.

These data points are then extrapolated into longitudinal strain calibration curves which are plotted in the form of a series of curves (FIG. 6) or a three-dimensional surface (FIGS. 7-8). Each of these plots is considered to be calibration datum within the meaning of the present invention. The calibration datum, so generated, then may be used to determine biaxial stresses in a steel component having metallurgical properties similar to the test piece 10 from which the calibration datum was generated.

It may be convenient to produce, from the longitudinal calibration curves of FIG. 6, a biaxial calibration surface as illustrated by FIGS. 7 and 8. The biaxial calibration surface graphically depicts the interdependence referred to above of Barkhausen noise levels (expressed in MP units), transverse strain or stress, and longitudinal strain or stress. As will be apparent from the Examples below, a biaxial calibration surface is a convenient instrumentality for making biaxial stress determinations in accordance with the present invention; the biaxial calibration surface likewise is a calibration datum within the scope of the present invention.

Although the biaxial calibration surface of FIGS. 7 and 8 was created from the longitudinal calibration curves of FIG. 6, it is envisioned that a biaxial calibration surface could be produced directly from the experimental data generated from test piece 10 through the use of well-known computer plotting techniques. The computer-assisted creation of a biaxial calibration surface would be possible in the case of static loading of test piece 10 as well as in a situation where test piece 10 is dynamically loaded in both transverse and longitudinal directions, and MP and the outputs of the strain gages are continuously sensed. Both of these techniques for loading test piece 10 and generating usable measurements therefrom are deemed to be within the skill of the art.

A biaxial calibration surface may be defined by the expression:

$$S(L,T) = f\{MP(L), \epsilon_L, \epsilon_T\} \quad (11)$$

where
S(L,T) = calibration surface
MP(L) = magnetoelastic parameter proportional to the level of Barkhausen noise, measured in longitudinal direction within a specific frequency range
$\epsilon_L$ = longitudinal strain
$\epsilon_T$ = transverse strain In expression (11), $\epsilon_L$ corresponds to principal strain $\epsilon_1$ of (1) and $\epsilon_T$ to principal strain $\epsilon_2$ of (2). S(L,T) can be determined by independently varying strains in L and T directions within elastic limits and recording corresponding values of MP(L). Surfaces S(L,T) can also be expressed in terms of stresses $\sigma_L$, $\sigma_T$ simply by using equations (4) and (5) to convert strains into stresses.

Use Of Calibration Datum

What now follows by way of example is a description of the use of the biaxial strain calibration surface to determine with Barkhausen noise levels a specific combination of biaxial principal strains in an actual steel component. Example I is illustrative of the presence of relatively small transverse strains in one of the principal directions which results in relatively small corrections to the principal strains $\epsilon_1$, $\epsilon_2$. Example II, however, illustrates that errors of greater magnitude in the principal strains $\epsilon_1$, $\epsilon_2$ can result from uniaxial strain measurements that assume transverse strain acting at the principal directions is negligible.

EXAMPLE I

The selected test area on the steel component to be examined is cleaned to bare metal with fine sandpaper and the Barkhausen noise measuring parameters are set the same as those used in generating the calibration datum. The strain at elasticity limit for said steel has been predetermined to be 1800. The MP values corresponding to the principal strains $\epsilon_1$, $\epsilon_2$ at the test location are found by testing MP in different angles on the component surface. The highest reading of MP, which corresponds to $\epsilon_1$, is denoted $MP_1$ and has a value of 200. The lowest reading, which corresponds to $\epsilon_2$ and should be found at a direction 90° from the direction of $\epsilon_1$, is denoted $MP_2$ and has a value of 90.

By reference to FIG. 7, which is a predetermined calibration surface for the same steel grade, approximations $\epsilon_{11}$, $\epsilon_{21}$ for strains $\epsilon_1$, $\epsilon_2$ are found assuming a uniaxial stress condition with zero transverse strain. This is done by projecting the values of $MP_1$ and $MP_2$ to the calibration surface along the line $\epsilon_T=0$. By projecting the two points found on the calibration surface at $\epsilon_T=0$ transversely to the scale for longitudinal strain, $\epsilon_{11}$ is found to have a value of about $+1000$ and $\epsilon_{21}$ a value of about $-100$. Thus, the approximations $\epsilon_{11}$, $\epsilon_{21}$ have values of $+1000$, $-100$, respectively.

To correct the approximations $\epsilon_{11}$, $\epsilon_{21}$ for transverse strain, it is necessary to take into account the presence of transverse strain in the principal directions. In other words, approximation $\epsilon_{11}$ is corrected by the transverse strain $\epsilon_{21}$ by first finding the longitudinal slice of FIG. 6 corresponding to the value of $-100$ ($\epsilon_T = \epsilon_{21}$). By following that slice on the calibration surface to the projected value of MP$_1$ (i.e. 200, to the point designated A), and then following the transverse slice passing through point A to the longitudinal strain scale, $\epsilon_{12}$ is found to be about $+1100$.

Approximation $\epsilon_{21}$ is corrected in a similar manner by finding the longitudinal slice of FIG. 6 corresponding to the value of $+1000$ ($\epsilon_T = \epsilon_{11}$). By following that slice onto the calibration surface to the projected value of MP$_2$ (i.e. 90, to the point designated B, which is on an extrapolation of the calibration surface shown in FIG. 7) and then following the transverse slice passing through point B to the longitudinal strain scale, $\epsilon_{22}$ is found to be about $+200$.

Accordingly, the corrected values of $\epsilon_1$, $\epsilon_2$ are $+1100$, $+200$ instead of the values $+1000$, $-100$ found when assuming transverse stress at the principal directions is zero; in percentage terms, the errors are about 6 and 17 percent of the strain at elasticity limit for the steel being examined, respectively. These values of strain may be converted to values of stress using the conversion formulae (4), (5) above.

If needed, normal strain $\epsilon_3$ may be found by the expression:

$$\epsilon_3 - \frac{\nu}{1-\nu}(\epsilon_{12} + \epsilon_{22}) = -430 \; (\nu = 0.3)$$

If the material of the steel component under examination has pronounced texture, it is advisable to determine whether the calibration surfaces are different in the rolling and transverse directions. This determination is accomplished by switching the L and T directions. Using the average MP values obtained from the two calibration surfaces would reduce texture-induced error thereby to half.

EXAMPLE II

In this example, the MP values measured at the test location on a steel component are MP$_1$=200 and MP$_2$=50. By reference to FIG. 8, the approximation $\epsilon_{11}$, $\epsilon_{12}$, assuming zero transverse stress, is determined to have the values $+1000$, $-700$. By applying the correction procedure described in Example I, the corrected values of $\epsilon_1$, $\epsilon_2$ are found to be $\epsilon_{12} = +1500$ and $\epsilon_{22} = -1800$. It should be noted, as with Example I, point B is found to be on an extrapolation of the calibration surface shown in FIG. 8. These corrected values for $\epsilon_1$, $\epsilon_2$ represent errors of about 25 and 61 percent, respectively, of the strain at the elasticity limit for the steel being examined, compared with the values of strain that would have been relied upon if transverse stress in the principal directions had been neglected as is the case in conventional practice.

The significant advantage of the present invention to steel manufacturers and users is therefore apparent.

What is claimed is:

1. A method for determining biaxial stresses in a steel component comprising the steps of
   generating a calibration datum (i) from an experimental test piece having metallurgical properties similar to said steel component and (ii) within the elastic limits of said test piece, said calibration datum reflecting varying Barkhausen noise levels as both longitudinal and transverse strains in said test piece are varied from their zero values;
   measuring Barkhausen noise levels in the first and second principal directions at a selected location on said steel component; and
   using said calibration datum, converting said measured Barkhausen noise levels to values of longitudinal and transverse strain in said first and second principal directions at said selected location on said steel component.

2. A method as recited in claim 1 wherein:
   said calibration datum is a table of pairs of Barkhausen noise level readings at varying conditions of longitudinal and transverse strain on said test piece.

3. A method as recited in claim 1 wherein said measured Barkhausen noise levels are converted to values of longitudinal and transverse strain in the first and second principal directions by the steps of:
   applying values representative of said measured Barkhausen noise levels to said calibration datum at zero transverse strain to obtain an approximation of the values of strain in said first and second principal directions;
   by use of said calibration datum, correcting said approximation of strain in said first principal direction by applying thereto the transverse effect of said approximation of strain in said second principal direction; and
   by use of said calibration datum, correcting said approximation of strain in said second principal direction by applying thereto the transverse effect of said approximation of strain in said first principal direction.

4. A method as recited in claim 3 wherein:
   said calibration datum is a calibration surface.

5. A method as recited in claim 3 wherein:
   said calibration data is a series of longitudinal strain curves, each curve having a specified value of transverse strain.

* * * * *

UNITED STATES PATENT AND TRADEMARK OFFICE
CERTIFICATE OF CORRECTION

PATENT NO. : 4,977,373
DATED : Dec. 11, 1990
INVENTOR(S) : Seppo I. Tiitto

It is certified that error appears in the above-identified patent and that said Letters Patent is hereby corrected as shown below:

Col. 8, lines 11-28, before "By", return to left margin and indent.

Signed and Sealed this

Fourth Day of August, 1992

Attest:

DOUGLAS B. COMER

*Attesting Officer*  *Acting Commissioner of Patents and Trademarks*